US011643644B2

(12) United States Patent
Ghosh et al.

(10) Patent No.: US 11,643,644 B2
(45) Date of Patent: May 9, 2023

(54) METHODS AND DEVICES FOR SIMULTANEOUS OPTICAL IRRADIATION AND OSCILLATING MAGNETIC FIELD RADIATION OF A TARGET

(71) Applicant: Southeast Missouri State University, Cape Girardeau, MO (US)

(72) Inventors: Santaneel Ghosh, Cape Girardeau, MO (US); Somesree GhoshMitra, Cape Girardeau, MO (US); Jian Peng, Cape Girardeau, MO (US)

(73) Assignee: Southeast Missouri State University, Cape Girardeau, MO (US)

( * ) Notice: Subject to any disclaimer, the term of this patent is extended or adjusted under 35 U.S.C. 154(b) by 81 days.

(21) Appl. No.: 17/328,517

(22) Filed: May 24, 2021

(65) Prior Publication Data

US 2021/0277382 A1 Sep. 9, 2021

Related U.S. Application Data

(62) Division of application No. 15/279,577, filed on Sep. 29, 2016, now Pat. No. 11,046,947.

(60) Provisional application No. 62/235,803, filed on Oct. 1, 2015.

(51) Int. Cl.
| | |
|---|---|
| *C12N 13/00* | (2006.01) |
| *C12M 1/42* | (2006.01) |
| *C12M 1/00* | (2006.01) |
| *A61K 41/00* | (2020.01) |
| *A61N 2/00* | (2006.01) |
| *A61N 5/06* | (2006.01) |
| *A61N 2/02* | (2006.01) |

(52) U.S. Cl.
CPC .............. *C12N 13/00* (2013.01); *A61K 41/00* (2013.01); *C12M 31/10* (2013.01); *C12M 35/06* (2013.01); *A61N 2/002* (2013.01); *A61N 2/006* (2013.01); *A61N 2/02* (2013.01); *A61N 5/0622* (2013.01); *A61N 2005/0651* (2013.01); *A61N 2005/0662* (2013.01)

(58) Field of Classification Search
None
See application file for complete search history.

(56) References Cited

U.S. PATENT DOCUMENTS

| | | | |
|---|---|---|---|
| 7,951,061 B2 | 5/2011 | Foreman et al. | |
| 11,077,191 B2 | 8/2021 | Ghosh et al. | |
| 2005/0089993 A1 | 4/2005 | Boccazzi et al. | |
| 2005/0090732 A1 | 4/2005 | Ivkov et al. | |
| 2006/0099146 A1 | 5/2006 | Chow et al. | |
| 2014/0243733 A1* | 8/2014 | McKenna | A61N 2/004 604/20 |
| 2014/0330257 A1 | 11/2014 | Hyde et al. | |

OTHER PUBLICATIONS

Di Corato, Riccardo et. al. Combining Magnetic Hyperthermia and Photodynamic Therapy for Tumor Ablation with Photo-responsive Magnetic Liposomes. American Chemical Society. vol. 9 No. 3. pp. 2904-2916. (Year: 2015).*
Jaque, D. et al. Nanoparticles for photothermal therapies. Nanoscale, 2014 (6). pp. 9494-9530. (Year: 2014).*
Adams et al., "Increasing magnetite contents of polymeric magnetic particles dramatically improves labeling of neural stem cell transplant populations," Nanomedicine Nanotechnology, Biology and Medicine, 2015, vol. 11, pp. 19-29.
Alkilany et al., "Gold nanorods: Their potential for photothermal therapeutics and drug delivery, tempered by the complexity of their biological interactions," Advanced Drug Delivery Reviews, 2011, pp. 1-10.
Di Corato et al., "Combining Magnetic Hyperthermia and Photodynamic Therapy for Tumor Ablation with Photoresponsive Magnetic Liposomes", American Chemical Society, 2015, vol. 9, No. 3., pp. 2904-2916.
Fortin et al., Size-sorted anionic iron oxide nanomagnets as colloidal mediators for magnetic hyperthermia, J. Am. Chem. Soc., 2007, vol. 129, pp. 2628-2635.
Ghosh et al., "Alternating Magnetic Field Controlled, Multifunctional Nano-Reservoirs: Intracellular Uptake and Improved Biocompatibility," Nanoscale Res. Lett., 2010, vol. 5, 10 pages.
Ghoshmitra et al., "Excellent biocompatibility of semiconductor quantum dots encased in multifunctional poly (N-isopropylacrylamide) nanoreservoirs and nuclear specific labeling of growing neurons," Applied Physics Letters, 2011, vol. 98, 103702.
Ghoshmitra et al., "Role of Engineered nanocarriers of axon regeneration and guidance: Current status and future trends," Advanced Drug Delivery Reviews, 2012, vol. 64, pp. 110-125.
Ghoshmitra et al., "Moderate Level Exposure to Magnetic Nanodots Encased in Tunable Poly(ethylene glycol) Analouge Biopolymer Shell Do Not Deleteriously Affect Neurite Outgrowth," Journal of Nanoscience and Nanotechnology, 2013, vol. 13, pp. 1-8.
Giuliani et al., "Low infra red laser light irradiation on cultured neural cells: effects on mitochondria and cell viability after oxidative stress," BMC Complementary and Alternative Medicine, 2009, vol. 9, No. 8, 10 pages.
Higuchi et al., "Visible light regulates neurite outgrowth of nerve cells," Cytotechnology, 2007, vol. 54, pp. 181-188.
Jaque et al., "Nanoparticles for photothermal therapies", Nanoscale, 2014, vol. 6, pp. 9494-9530.

(Continued)

*Primary Examiner* — Nghi V Nguyen
(74) *Attorney, Agent, or Firm* — Armstrong Teasdale LLP (57) ABSTRACT

An incubator-actuator device including a sample chamber, a magnetic field generating coil, and a light-emitting diode (LED) placement cage is provided herein. The incubator-actuator device is configured for simultaneous optical irradiation and oscillating magnetic field irradiation of a mammalian cell or a nanostructure. A system including an incubator-actuator device including a sample chamber, a magnetic field generating coil, and a light-emitting diode (LED) placement cage, and a laser is also provided herein. The system is configured for simultaneous optical irradiation and oscillating magnetic field irradiation of a target.

20 Claims, 4 Drawing Sheets

(56) References Cited

OTHER PUBLICATIONS

Kim et al., "Enhancement of neurite outgrowth in PC12 cells by iron oxide nanoparticles," Biomaterials, 2011, vol. 32, pp. 2871-2877.
Kumar et al., "Magnetic Nanomaterials for Hyperthermia-based Therapy and Controlled Drug Delivery," Advanced Drug Delivery Reviews, 2011, 20 pages.
McCallister et al., "Engineered, thermoresponsive, magnetic nanocarriers of oligo (ethylene glycol)-methacrylate-based biopolymers," Applied Physics Express, 2014, vol. 7, 117003.
Purushotham et al., "Thermoresponsive magnetic composite nanomaterials for multimodal cancer therapy," Acta Biomaterialia, 2010, vol. 6, pp. 502-510.
Setua et al., "Cisplatin-tethered gold nanospheres for multimodal chemo-radiotherapy of glioblastoma," Nanoscale, 2014, vol. 6, pp. 10865-10873.

* cited by examiner

METHODS AND DEVICES FOR SIMULTANEOUS OPTICAL IRRADIATION AND OSCILLATING MAGNETIC FIELD RADIATION OF A TARGET

CROSS-REFERENCE TO RELATED APPLICATION

This application is a divisional of U.S. patent application Ser. No. 15/279,577 filed Sep. 29, 2016, which claims priority from U.S. Provisional Application No. 62/235,803, filed Oct. 1, 2015. These applications are incorporated herein in their entireties.

FIELD OF THE DISCLOSURE

The present disclosure is generally directed to methods and devices for the precise and simultaneous optical irradiation and oscillating magnetic field radiation of a target, such as mammalian cells and/or nanostructures.

BACKGROUND OF THE DISCLOSURE

Light therapy, when administered through a particular emission mode, is capable of eliciting biological effects and thus is used as a class therapeutic modality. Further, nanostructures made from materials with magnetic properties are attractive possibilities for designing novel nano-platforms for therapeutic applications, with the help of remotely tunable magnetic actuation processes.

Remote-controlled magnetic actuation techniques for various nano-devices can be broadly categorized in two different types: (a) static or direct current (DC) magnetic field dependent actuation, and (b) oscillating, or alternating current (AC) magnetic field induced actuation. The application of the static or gradient magnetic field has been performed primarily in the areas of magnetic separation, magnetic force based immunoassay, magnetic force-based neurite elongation from the model neuronal cells, and for localization/targeting of the magnetic nanostructures in the intracellular environment. On the other hand, oscillating magnetic field based actuations have been performed in the areas of magnetic hyperthermia for potential cancer treatment, controlled release of therapeutic agents into or near the target cells, and to modulate the intracellular pathways for controlling various cellular functions.

Since both optical and magnetic actuation can modulate the cellular pathways individually, but have their respective individual drawbacks, there is a need to augment the effectiveness of these approaches by aptly combining the optical and the magnetic actuation, especially in the field of tissue repair/regeneration or in cancer treatment. The present disclosure achieves this goal by using a highly specific and novel set-up of a device for precise and simultaneous optical irradiation and oscillating magnetic field radiation of mammalian cells that enables one to conduct, modulate, and fine-tune simultaneous optical and AC magnetic field exposure and actuation of cultured mammalian cells and/or nanostructures.

SUMMARY OF THE DISCLOSURE

In one aspect of the present disclosure, an incubator-actuator device for simultaneous optical irradiation and oscillating magnetic field irradiation of a mammalian cell is disclosed. The device comprises: a sample chamber, a magnetic field generating coil, and, a light-emitting diode (LED) placement cage; wherein the optical irradiation comprises exposing the mammalian cell to gold nanoparticle induced photo-thermal optical irradiation having a laser power of 300 mW; wherein the oscillating magnetic field irradiation comprises exposing the mammalian cell to oscillating magnetic field radiation, wherein the magnetic field has an intensity of from 40 Oe to 60 Oe, and wherein the magnetic field has a frequency of 120 kHz; and wherein the simultaneous optical irradiation and oscillating magnetic field irradiation occur within the incubator-actuator device.

In another aspect of the present disclosure, an incubator-actuator device for simultaneous optical irradiation and oscillating magnetic field irradiation of a nanostructure is disclosed. The device comprises: a sample chamber, a magnetic field generating coil, and, a light-emitting diode (LED) placement cage; wherein the optical irradiation comprises exposing the nanostructure to gold nanoparticle induced photo-thermal optical irradiation having a laser power of 300 mW; wherein the oscillating magnetic field irradiation comprises exposing the nanostructure to oscillating magnetic field radiation, wherein the magnetic field has an intensity of from 40 Oe to 60 Oe, and wherein the magnetic field has a frequency of 120 kHz; and wherein the simultaneous optical irradiation and oscillating magnetic field irradiation occur within the incubator-actuator device.

In yet another aspect of the present disclosure, a system for simultaneous optical irradiation and oscillating magnetic field radiation of a target is disclosed. The system comprises: an incubator-actuator device comprising a sample chamber, a magnetic field generating coil and a light-emitting diode (LED) placement cage; and, a laser; wherein the optical irradiation comprises exposing the target to gold nanoparticle induced photo-thermal optical irradiation having a laser power of 300 mW; wherein the oscillating magnetic field irradiation comprises exposing the target to oscillating magnetic field irradiation, wherein the magnetic field has an intensity of from 40 Oe to 60 Oe, and wherein the magnetic field has a frequency of 120 kHz; wherein the simultaneous optical irradiation and oscillating magnetic field irradiation occur within the incubator-actuator device; and wherein the target is selected from at least one of a mammalian cell and a nanostructure.

DETAILED DESCRIPTION OF THE DISCLOSURE

In the present disclosure, the inventors have found a way, for example through the development of novel nanoparticles, which can potentially carry a photo/magnetic stimulative effect on tissue repair or neuronal growth and guidance, to elicit significant biological effects. More specifically, the inventors have created devices and methods that simultaneously regulate the optical and magnetic stimulation to treat various therapeutic conditions and achieve a combinatorial treatment. The devices are used for simultaneous optical and magnetic stimulation of a target, such as a cell, and, further, are used in combination with the delivery of externally tunable nanostructures. The devices/methods present an alternative to other treatment methods, such as, for example, low level laser therapy.

In some embodiments disclosed herein, mammalian cells are simultaneously exposed to varying combinations of optical and oscillating magnetic field excitation—thereby creating synergistic actuation strategies that combine and augment the positive outcomes of opto-magnetic excitation and nano-vector stimulation on intracellular pathways. This strategy is effective in axon growth and neural circuit reconstruction research, or, in efficient killing of cancer cells. The idea is further implemented to perform the nanoscale energy transfer to the targeted cells. Such a framework also controls intracellular functions by controlling the flow of the excitation energy on the cells. These results may change treatment potentials for diseases that involve endothelium damage if used appropriately.

In accordance with the present disclosure, the responses (e.g., specific absorption rate or SAR) of magnetic or optically responsive nanostructures exposed to simultaneous optical and oscillating magnetic field excitations are characterized and quantified. Moreover, the release profile of various drug/protein molecules from various smart micro- or nano-structures under the influence of opto-magnetic actuation is assessed.

Previously known methods, such as magnetic hyperthermia of model cells, low level laser/LED therapy, or photothermal delivery of nanostructures/therapeutic agents are performed in one set-up in accordance with the present disclosure.

The present disclosure is thus directed to devices and methods for the precise and simultaneous optical irradiation and magnetic field radiation of mammalian cells and/or nanostructures.

As used herein, "radiation" refers to the emission or transmission of energy in the form of waves or particles through space or through a material medium. These include, for example, electromagnetic radiation (also known as "continuum radiation"), gamma rays, radio waves, visible light and x-rays. Particle radiation, such as, for example, alpha-, beta- and neutron radiation (discrete energy per particle) is also covered under the term. Further, acoustic radiation, such as, for example, ultrasound, sound, and seismic waves (dependent on intervening mass for transmission) are included under the term as well.

As used herein, the term "irradiation" refers to the therapeutic or diagnostic use of radiation. Irradiation refers generally to optical illumination.

In one embodiment, a method for irradiation of a mammalian cell is disclosed, the method comprises exposing the cell to optical irradiation and simultaneously exposing the cell to oscillating magnetic field radiation.

In some embodiments, the simultaneous optical irradiation and oscillating magnetic field radiation occurs within an incubator-actuator device.

The incubator-actuator device conducts simultaneous optical irradiation and magnetic field radiation of cells, such as mammalian cells, as well as nanostructures. The device comprises a sample chamber, a magnetic field generating coil, and a light-emitting diode (LED) placement cage. In some embodiments, the device further comprises a glass window, a fiber optic thermometer, a laser irradiation path, a temperature controlling unit, and combinations thereof. In some embodiments, the temperature controlling unit controls the temperature within the device to be from about 15° C. to about 50° C., from about 20° C. to about 40° C., or from about 23° C. to about 37° C.

The present disclosure is also directed to a system for the simultaneous optical irradiation and oscillating magnetic field radiation of a cell, such as a mammalian cell, and/or a nanostructure. The system comprises an incubator-actuator device comprising a sample chamber, a magnetic field generating coil and an LED placement cage; and, a laser.

In some embodiments, the system further comprises a beam expander, a laser stop, a function generator, an oscilloscope, an amplifier, a heating unit, a computer, a laser power source, a temperature probe, and combinations thereof. In some embodiments, the device of the system further comprises a glass window, a fiber optic thermometer, a laser irradiation path, a temperature controlling unit, and combinations thereof. The temperature controlling unit of the device in the system controls the temperature within the device to be from about 15° C. to about 50° C., from about 20° C. to about 40° C., or from about 23° C. to about 37° C. In some embodiments, the temperature is controlled for various nanoscale characterizations, especially in the area of microfluidics and/or drug delivery, where the release of several therapeutic agents are performed between room and physiological temperatures.

The sample chamber holds tissue culture tubes. Inside the sample chamber, in some embodiments, B35 neuroblastoma cells/PC12 cells are cultured and/or nano-carriers are colloidally dispersed. In some embodiments, the glass window is a high performance glass window located at a front wall of the device for transmitting the laser irradiation during moderate/high level optical stimulation.

In some embodiments, a circuit is used and the circuit utilizes a capacitor bank in series with an inductor coil and a 0.5 ohm resistor. The magnetic field is modified by changing the capacitor and/or the coil inductance.

The device further comprises a top and a bottom panel that are removable, which allows the samples within the chamber to be switched. In some embodiments, the device is attached to a base of the laser. In some embodiments, black absorbent tape material is used to confine the laser exposure to specific areas. In some embodiments, the electronics and the laser system are mounted at a distance from the incubator to prevent and/or mitigate potential interferences that create fluctuations of the magnetic field intensity during measurements.

In accordance with the present disclosure, in some embodiments, the beam expander expands the beam diameter that is directly coming from the laser (to minimize damage from laser irradiation), the laser produces optical excitation to the target(s) (e.g., AuNPs) for remote heating, the function generator generates different types of electrical waveforms over a wide range of frequencies, the computer records sample (nanocarrier or mammalian cell culture media) temperature responses during optical-AC magnetic field combined (or separate) actuation, as well as reading other responses, for example—light intensity, temperature inside the incubator during experiment, etc.; and, the oscilloscope displays and analyzes the waveform of electronic signals.

Figure 1:
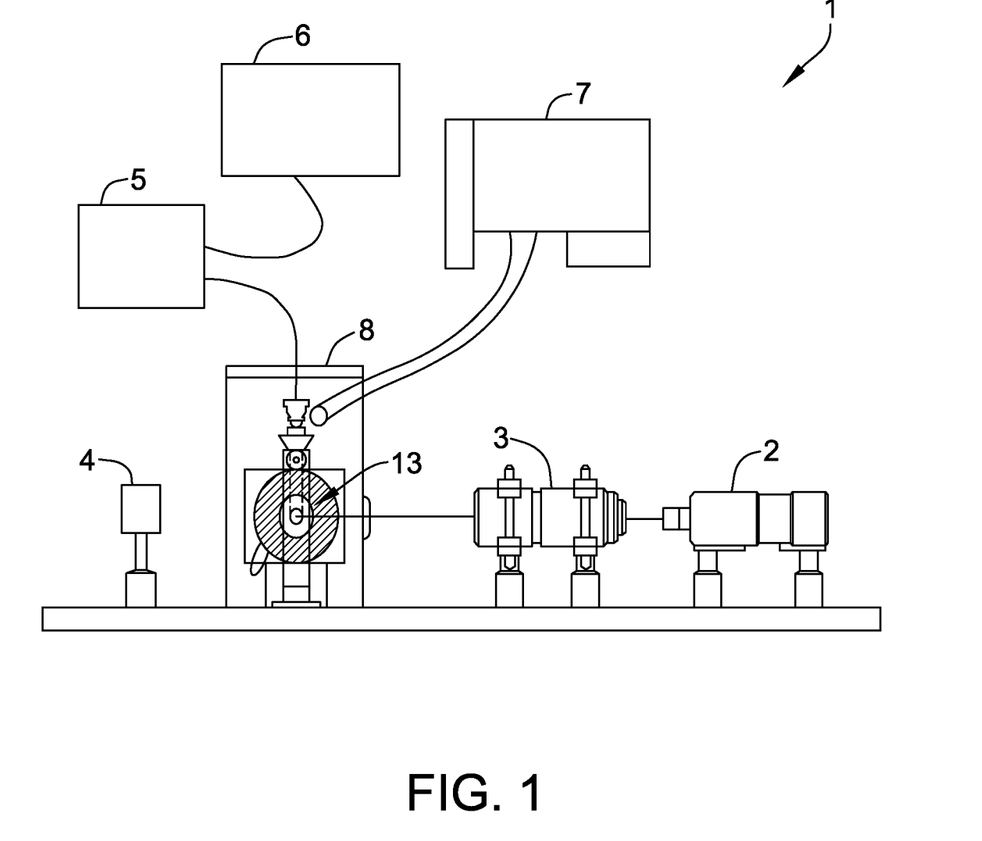
FIG. 1 is an exemplary embodiment of a device for generating combinations of magnetic and optical stimulation in accordance with the present disclosure.
Figure 3:
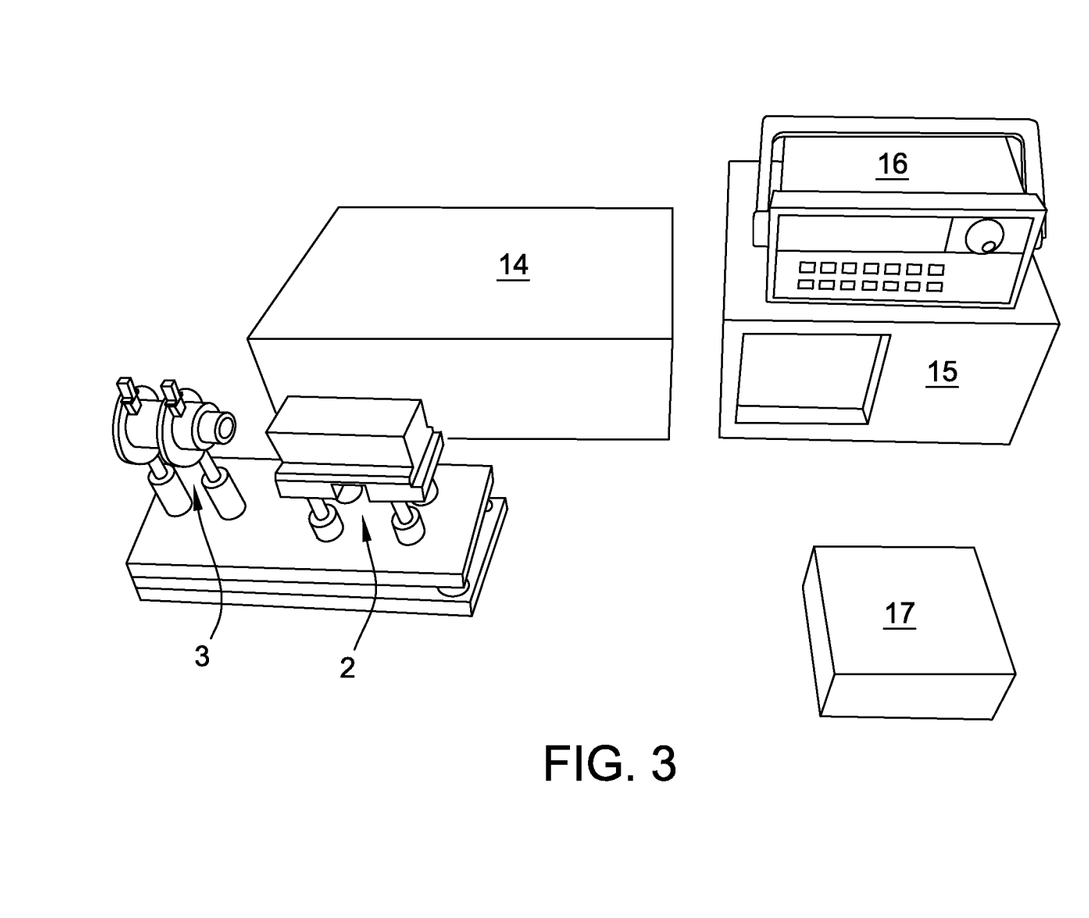
FIG. 3 is an exemplary embodiment of a device for generating combinations of magnetic and optical stimulation in accordance with the present disclosure.

FIG. 1 is an exemplary embodiment of a system 1 in accordance with the present disclosure. The system 1 comprises a laser 2, a beam expander 3, a laser stop 4, a temperature probe 5, a computer 6, a heating element 7 and an incubator-actuator device 8. The device 8 comprises an AC/DC magnetic field generator 13. FIG. 3 is another exemplary embodiment of components of a system in accordance with the present disclosure, the system comprising a laser 2, a beam expander 3, an amplifier 14, an oscilloscope 15, a function generator 16, and a laser power source 17.

Figure 2:
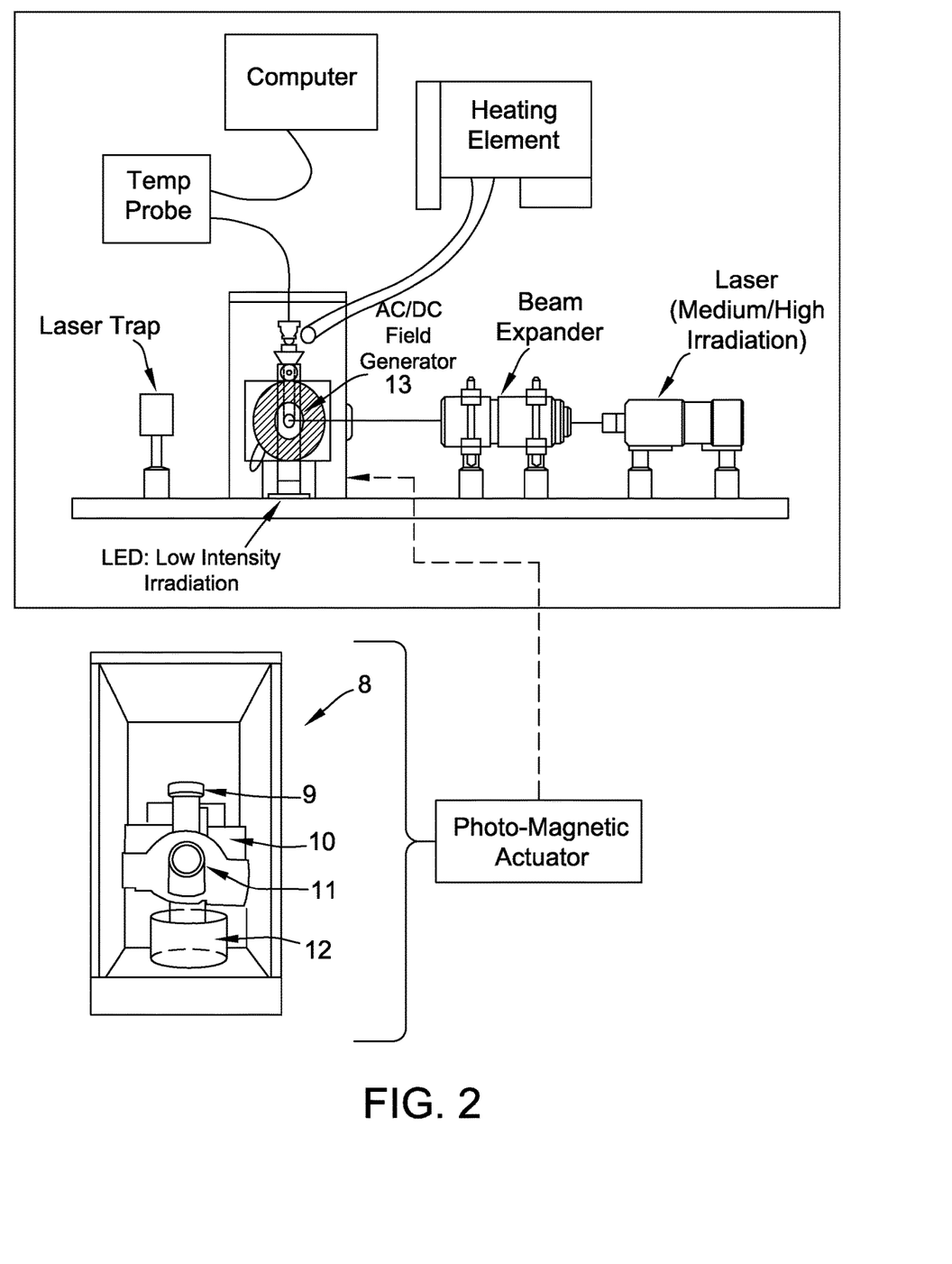
FIG. 2 is an exemplary embodiment of a device for generating combinations of magnetic and optical stimulation in accordance with the present disclosure.

FIG. 2 is an exemplary embodiment of the incubator-actuator device 8 as a component of the system 1. The device 8 comprises a sample chamber 9, an AC/DC magnetic field generating coil 10, a laser irradiation path 11, and an LED placement cage 12.

In operation, the laser exposes a target to optical irradiation. The target can be, for example, a mammalian cell and/or a nanostructure. In some embodiments, the laser travels through a beam expander. In some embodiments, after travelling through the beam expander and irradiating the target, the laser hits a laser stop, which prevents the laser from further moving.

In some embodiments of the present disclosure, the optical irradiation is selected from the group consisting of LED-induced optical irradiation, ultraviolet-visible-induced optical irradiation, near infra-red (NIR)-induced optical irradiation, and combinations thereof. In some embodiments, the optical irradiation has an intensity of less than about 2 mW/cm$^2$. In other embodiments, the optical irradiation has an intensity of from about 0 mW/cm$^2$ to about 1,000 mW/cm$^2$, or from about 2 mW/cm$^2$ to about 1,000 mW/cm$^2$. In some embodiments, the optical irradiation occurs at a wavelength between about 450 nm to about 675 nm, between about 450 nm to about 500 nm, or between about 620 nm to about 660 nm.

The optical irradiation range can be altered by a user by selecting a less or more powerful light irradiation source. For LED irradiation, in some embodiments, the range is increased by order of magnitude (e.g., at least up to 20 mW/cm$^2$) by reducing the distance between the LED source and the sample chamber.

In some embodiments, for example for cancer cell destruction, a higher intensity (more than about 50 mW of laser power) is used. For neural regeneration or wound healing, micro watts or less than about 2 mW/cm$^2$ optical intensities are used. For neural regeneration, wavelengths of from about 450 nm to about 675 nm, between about 450 nm to about 500 nm, or between about 620 nm to about 660 nm are used.

In some embodiments of the present disclosure, the laser has a power of from about 100 mW to about 500 mW, from about 200 mW to about 400 mW, or from about 250 mW to about 350 mW.

In addition to the optical irradiation that is being applied to the target, the target is also simultaneously exposed to an oscillating magnetic field radiation. In some embodiments, the magnetic field has an intensity of from about 0 Oe to about 150 Oe, from about 0 Oe to about 20 Oe, from about 10 Oe to about 150 Oe, or from about 40 Oe to about 60 Oe. In some embodiments, the magnetic field has a frequency of from about 0 kHz to about 1000 kHz, from about 50 kHz to about 500 kHz, from about 60 kHz to about 200 kHz, or from about 200 kHz to about 400 kHz.

In another aspect of the present disclosure, the target to be simultaneously exposed to the optical irradiation and the magnetic field radiation is a nanostructure. In particular, a method is disclosed for irradiation of a nanostructure, wherein the method comprises exposing the nanostructure to optical irradiation and simultaneously exposing the nanostructure to oscillating magnetic field radiation.

In some embodiments, the method of irradiation of the nanostructure occurs with an incubator-actuator device as described elsewhere throughout this application, including the various embodiments disclosed throughout this application.

In some embodiments, the nanostructures comprise a shell encapsulating at least one nanoparticle. The shell comprises a material selected from the group consisting of polyvinylpyrrolidone (PVP), polyethylene glycol (PEG) and derivatives thereof, poly(N-isopropylacrylamide), tannic acid, dextran, dimercaptosuccinic acid (DMSA) and combinations thereof.

In some embodiments, the at least one nanoparticle is at least one magnetic nanoparticle. In some embodiments, the at least one magnetic nanoparticle comprises at least one of gold, ferric oxide, magnetite, maghemite, gadolinium-doped cobalt ferrite, and combinations thereof.

In some embodiments, the shell comprises PVP and the at least one nanoparticle comprises gold. In some embodiments, the shell has a thickness of from about 2 nm to about 200 nm, from about 5 nm to about 50 nm, from about 40 nm to about 150 nm, or from about 2 nm to about 10 nm.

In some embodiments, the shell encapsulates a single nanoparticle or multiple nanoparticles. In some embodiments, the at least one nanoparticle has a size of from about 5 nm to about 100 nm, or from about 8 nm to about 20 nm. In some embodiments, the at least one nanoparticle has a diameter of from about 5 nm to about 270 nm, from about 5 nm to about 10 nm, or from about 210 nm to about 270 nm.

In some embodiments of the present disclosure, the shell has at least one additive loaded or attached thereon. In some embodiments, the at least one additive is a drug molecule. In some embodiments, the nanostructures release a therapeutic agent, and methods disclosed herein include measuring a release profile of a therapeutic agent from the nanostructures. The methods also further include characterizing a nanostructure response to the simultaneous optical irradiation and magnetic field radiation. The methods disclosed herein further include quantifying a nanostructure response to the simultaneous optical irradiation and oscillating magnetic field radiation.

In some embodiments, a PEG analogue based core-shell magnetic nano-reservoir system is disclosed. The system is based on ferromagnetic nanoparticles encapsulated within a thermo-activated polymer network that is non-toxic, anti-immunogenic and possesses a higher Young's modulus than other polymer networks, such as, for example, a poly(N-isopropylacrylamide) (PNIPAM) network system. The polymeric shell acts as a reservoir, for example, for drug molecules, while the magnetic core is a nano-source of heat. Thus, the release of imbibed drug molecules is initiated from the tunable excipient by causing volumetric shrinkage of the polymer network when exposed to the oscillating magnetic field.

In some embodiments, to generate the simultaneous optical stimulation, colloidally stable gold nanoparticles (AuNPs) having a particle size of from about 10 nm to about 50 nm, from about 15 nm to about 35 nm, about 10 nm, or about 20 nm are used. These AuNPs are selected with absorption peaks near about 520 nm. The incubator-actuator device of the present disclosure generates an alternating magnetic field with varying intensity and frequency range and optical irradiation into the target cell culture media when the power source is switched on.

The relaxation losses of the thermos-responsive core-shell nanostructures are then quantified. Field and frequency dependent temperature modulation of the target cells demonstrated the loss mechanism primarily related to the Brown relaxation. In some embodiments, optically induced losses from the gold nanoparticles were precisely regulated using a nanoparticle concentration of from about 2 µg/mL to about 10 µg/mL, or about 6 µg/mL in the culture media. As a result, magnetic and optical induced heating were performed using the same device inside the reaction vessel. For these excitations, temperature changes ranging from about 1° C. to about 5° C., or about 3° C. were achieved, and the temperatures were regulated within about 1° C. by modulating magnetic field, frequency and/or optical irradiation. The ability to induce controlled localized magnetic and optical actuation while allowing sustained release of therapeutic agents from the nanocarriers makes this system attractive for various biomedical applications, especially for tumor regression, wound healing or neuronal regeneration therapy.

In some embodiments of the present disclosure, the simultaneous optical irradiation and magnetic field radiation has a therapeutic application to the target, such as, for example, a mammalian cell. In some embodiments, the therapeutic application to the target is selected from the group consisting of tissue repair, wound healing, neural regeneration, neural circuit reconstruction, destroying cancer cells, regulating cell proliferation, regulating cell differentiation, tumor regression, facilitating neurite outgrowth of nerve cells, repairing endothelial cells, release profile of a drug, and combinations thereof.

In some embodiments, the following therapeutic applications and approaches are disclosed: combined (optical and AC magnetic field) hyperthermia at low, moderate, and high intensities for cancer cells; low level photo-magnetic exposure (therapy) for wound healing applications; low level photo-magnetic stimulation (to facilitate neurite outgrowth) of nerve cells; photo-magnetic exposure (i.e., nano-scale photo-magnetic energy exposure) of damaged endothelial cells; characterizing and quantifying the responses (e.g., specific absorption rate or SAR) of magnetic or optically responsive nanostructures exposed to simultaneous optical and oscillating magnetic field excitations; release profile of various drugs (for example—cancer drugs for chemotherapy, therapeutic proteins) that are loaded inside the polymeric nanoparticles or other smart nanostructures; and combinations thereof.

The types of mammalian cells that can be used for various experiments include (but are not limited to) the following: various cancer cells, model neuronal cells, such as, for example, PC12 and various primary neurons, endothelial cells, and fibroblasts, etc.

EXAMPLES

The following examples describe or illustrate various embodiments of the present disclosure. Other embodiments within the scope of the appended claims will be apparent to a skilled artisan considering the specification or practice of the disclosure as described herein. It is intended that the specification, together with the examples, be considered exemplary only, with the scope and spirit of the disclosure being indicated by the claims, which follow the examples.

Example 1

In this example, the effect of magnetic field intensity in combination with a constant frequency on mammalian cells in culture was studied. The device used for the example was an incubator-actuator device in accordance with the present disclosure that generated an alternating magnetic field with varying intensity into the target. A polyethylene glycol (PEG) analogue-based core-shell magnetic nano-reservoir system was designed.

Three sample targets were the focus of the example: (1) 400 µg/ml of magnetic nanoparticles (MNPs); (2) 200 µg/ml of MNPs; and, (3) deionized water. The MNPs were ferromagnetic nanoparticles encapsulated within a thermo-activated polymer network that is non-toxic, anti-immunogenic and possesses a higher Young's modulus. The sample targets were subjected to magnetic field intensities of 40 Oe and 60 Oe, respectively, with the magnetic field radiation frequency constant at 120 kHz. The targets were suspended in cell culture PC 12 neuronal model media.

Figure 4A:
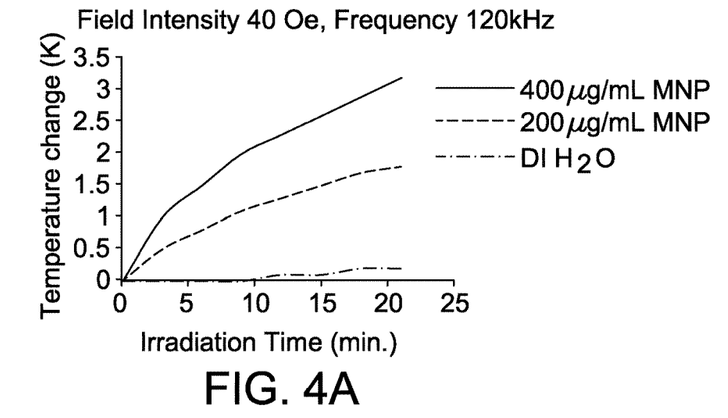
FIG. 4A is an exemplary embodiment of the effect of irradiation time and temperature on a sample in accordance with the present disclosure.

FIG. 4A is a graphical depiction of the results of an oscillating magnetic field radiation of the targets at a field intensity of 40 Oe and a frequency of 120 kHz measured as the temperature change (K) of the targets over irradiation time (minutes). As can be seen from FIG. 4A, as the irradiation time of the targets increased, the temperature change increased as well for the two MNP samples, but not for the deionized water sample (which had minimal to no temperature increase). The sample with the highest MNP concentration (i.e., 400 µg/ml) had the greatest increase in temperature change.

Figure 4B:
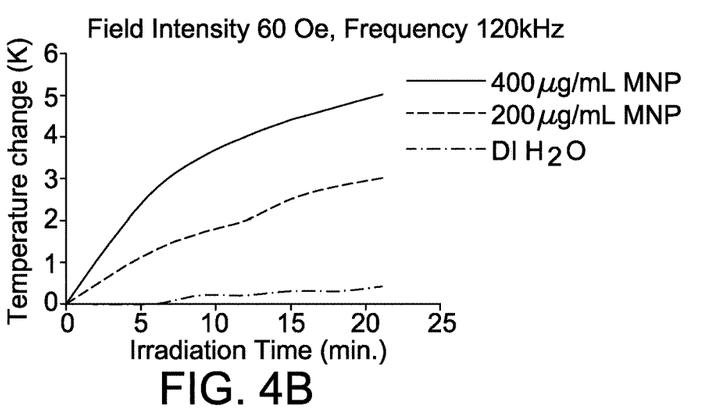
FIG. 4B is an exemplary embodiment of the effect of irradiation time and temperature on a sample in accordance with the present disclosure.

FIG. 4B is a graphical depiction of the results of an oscillating magnetic field radiation of the targets at a field intensity of 60 Oe and a frequency of 120 kHz measured as the temperature change (K) of the targets over irradiation time (minutes). As can be seen from FIG. 4B, as the irradiation time of the targets increased, the temperature change increased as well for the two MNP samples, but not for the deionized water sample (which had minimal to no temperature increase). The sample with the highest MNP concentration (i.e., 400 µg/ml) had the greatest increase in temperature change.

As can be seen in the comparison of FIG. 4A to 4B, an increase in the field intensity from 40 Oe to 60 Oe led to an increased temperature in the samples tested. The temperatures were regulated within plus or minus 1° C. by modulating the magnetic field and/or frequency.

Example 2

In this example, the effect of a simultaneous optical irradiation and magnetic field radiation on mammalian cells in culture was studied. The device used for the example was an incubator-actuator device in accordance with the present disclosure that generated an alternating magnetic field with varying intensity into the target. A polyethylene glycol (PEG) analogue-based core-shell magnetic nano-reservoir system was designed.

Three sample targets were the focus of the example: (1) 4 µg/ml of gold nanoparticles (AuNPs); (2) 2 µg/ml of AuNPs; and, (3) deionized water. The AuNPs were colloidally stable AuNPs with a particle size of about 10 nm and absorption peaks near about 520 nm. The sample targets were subjected to an optical irradiation at a laser power of 300 mW. In the second set of samples, however, the AuNP targets were combined with various concentration levels of MNPs, such that the targets had the following makeup: 1) 2 µg/ml of AuNPs and 400 µg/ml of MNPs; (2) 2 µg/ml of AuNPs and 200 µg/ml of MNPs; and, (3) deionized water. The MNPs were ferromagnetic nanoparticles encapsulated within a thermo-activated polymer network that is non-toxic, anti-immunogenic and possesses a higher Young's modulus. Further, the second set of sample targets were subjected to a simultaneous exposure to both the 300 mW of optical laser irradiation and 60 Oe of a magnetic field radiation intensity. The targets were suspended in cell culture PC 12 neuronal model media.

Figure 4C:
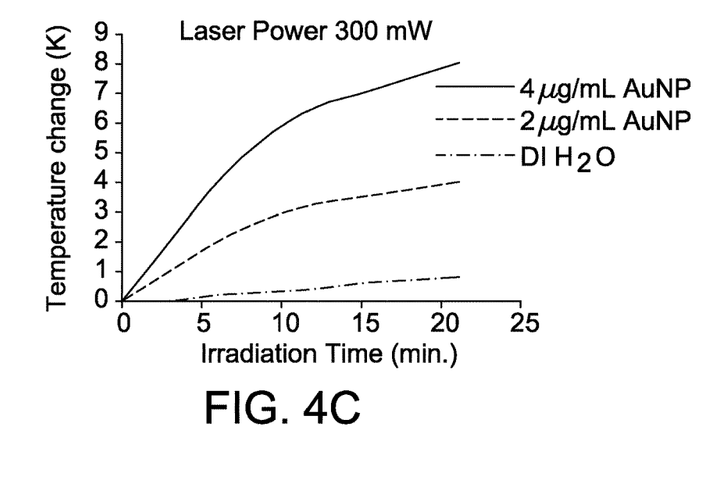
FIG. 4C is an exemplary embodiment of the effect of irradiation time and temperature on a sample in accordance with the present disclosure.

FIG. 4C is a graphical depiction of the results of an optical irradiation of the targets at a laser power of 300 mW measured as the temperature change (K) of the targets over irradiation time (minutes). As can be seen from FIG. 4C, as the irradiation time of the targets increased, the temperature change increased as well for the two AuNP samples, but not for the deionized water sample (which had minimal to no temperature increase). The sample with the highest AuNP concentration (i.e., 4 μg/ml) had the greatest increase in temperature change.

Figure 4D:
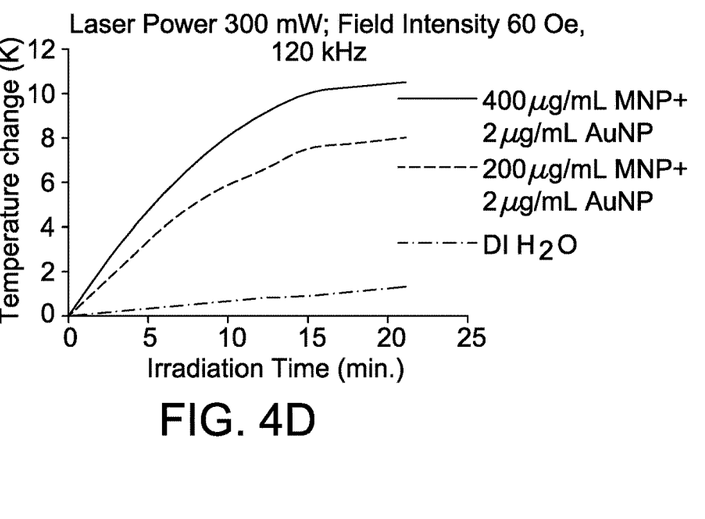
FIG. 4D is an exemplary embodiment of the effect of irradiation time and temperature on a sample in accordance with the present disclosure.

FIG. 4D is a graphical depiction of the results of a simultaneous optical irradiation (laser power of 300 mW) and magnetic field radiation (field intensity of 60 Oe) measured as the temperature change (K) of the targets over irradiation time (minutes). As can be seen from FIG. 4D, as the irradiation time of the targets increased, the temperature change increased as well for the two AuNP/MNP samples, but not for the deionized water sample (which had minimal to no temperature increase). The sample with the highest MNP concentration (i.e., 400 μg/ml) had the greatest increase in temperature change.

As can be seen in the comparison of FIG. 4C to 4D, a significant increase in temperature occurred for the 200 μg/ml MNP sample that included 2 μg/ml of AuNPs. Moreover, as compared to the samples that include just the AuNPs, the addition of MNPs to the AuNPs resulted in an increase in temperature change as well, especially with respect to the 2 μg/ml sample. Thus, the combined actuation yielded a greater temperature change in the culture media. By tuning the intensity of the magnetic field and optical irradiation, cell proliferation and/or differentiation was regulated.

EQUIVALENTS AND SCOPE

In view of the above, it will be seen that the several advantages of the disclosure are achieved and other advantageous results attained. As various changes could be made in the above processes and composites without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. It is also noted that the terms "comprising", "including", "having" or "containing" are intended to be open and permits the inclusion of additional elements or steps.

What is claimed is:

1. An incubator-actuator device comprising:
a sample chamber,
a magnetic field generating coil, and,
a light-emitting diode (LED) placement cage;
wherein the incubator-actuator device is configured for simultaneous optical irradiation and oscillating magnetic field irradiation of a mammalian cell;
wherein the optical irradiation comprises exposing the mammalian cell to gold nanoparticle induced photo-thermal optical irradiation having a laser power of 300 mW;
wherein the oscillating magnetic field irradiation comprises exposing the mammalian cell to oscillating magnetic field radiation, wherein the magnetic field has an intensity of from 40 Oe to 60 Oe, and wherein the magnetic field has a frequency of 120 kHz; and
wherein the simultaneous optical irradiation and oscillating magnetic field irradiation occur within the incubator-actuator device.

2. The device of claim 1, wherein the gold nanoparticle induced photo-thermal optical irradiation occurs at a wavelength between about 450 nm to about 675 nm.

3. The device of claim 1, wherein simultaneously exposing the mammalian cell comprises simultaneously initiating both the gold nanoparticle induced photo-thermal optical irradiation and the oscillating magnetic field irradiation.

4. An incubator-actuator device comprising:
a sample chamber,
a magnetic field generating coil, and,
a light-emitting diode (LED) placement cage;
wherein the incubator-actuator device is configured for simultaneous optical irradiation and oscillating magnetic field irradiation of a nanostructure;
wherein the optical irradiation comprises exposing the nanostructure to gold nanoparticle induced photo-thermal optical irradiation having a laser power of 300 mW;
wherein the oscillating magnetic field irradiation comprises exposing the nanostructure to oscillating magnetic field radiation, wherein the magnetic field has an intensity of from 40 Oe to 60 Oe, and wherein the magnetic field has a frequency of 120 kHz; and
wherein the simultaneous optical irradiation and oscillating magnetic field irradiation occur within the incubator-actuator device.

5. The device of claim 4, wherein the gold nanoparticle induced photo-thermal optical irradiation occurs at a wavelength between about 450 nm to about 675 nm.

6. The device of claim 4, wherein simultaneously exposing the nanostructure comprises simultaneously initiating both the gold nanoparticle induced photo-thermal optical irradiation and the oscillating magnetic field irradiation.

7. The device of claim 4, wherein the nanostructure comprises a shell encapsulating at least one nanoparticle.

8. The device of claim 7, wherein the shell comprises a material selected from the group consisting of polyvinylpyrrolidone (PVP), polyethylene glycol (PEG) and derivatives thereof, poly(N-isopropylacrylamide), tannic acid, dextran, dimercaptosuccinic acid (DMSA) and combinations thereof.

9. The device of claim 7, wherein the at least one nanoparticle is at least one magnetic nanoparticle selected from the group consisting of gold, ferric oxide, magnetite, maghemite, gadolinium-doped cobalt ferrite, and combinations thereof.

10. The device of claim 7, wherein the shell has a thickness of from about 2 nm to about 200 nm.

11. The device of claim 7, wherein the at least one nanoparticle has a size of from about 5 nm to about 100 nm.

12. The device of claim 7, wherein the at least one nanoparticle has a diameter of from about 5 nm to about 270 nm.

13. A system comprising:
an incubator-actuator device comprising a sample chamber, a magnetic field generating coil and a light-emitting diode (LED) placement cage; and,
a laser;
wherein the system is configured for simultaneous optical irradiation and oscillating magnetic field radiation of a target;
wherein the optical irradiation comprises exposing the target to gold nanoparticle induced photo-thermal optical irradiation having a laser power of 300 mW;
wherein the oscillating magnetic field irradiation comprises exposing the target to oscillating magnetic field irradiation, wherein the magnetic field has an intensity of from 40 Oe to 60 Oe, and wherein the magnetic field has a frequency of 120 kHz;
wherein the simultaneous optical irradiation and oscillating magnetic field irradiation occur within the incubator-actuator device; and
wherein the target is selected from at least one of a mammalian cell and a nanostructure.

14. The system of claim 13, wherein the gold nanoparticle induced photo-thermal optical irradiation occurs at a wavelength between about 450 nm to about 675 nm.

15. The system of claim 13, wherein simultaneously exposing the target comprises simultaneously initiating both the gold nanoparticle induced photo-thermal optical irradiation and the oscillating magnetic field irradiation.

16. The system of claim 13, wherein the target is a nanostructure and the nanostructure comprises a shell encapsulating at least one nanoparticle.

17. The system of claim 16, wherein the shell has a thickness of from about 2 nm to about 200 nm, and wherein the shell comprises a material selected from the group consisting of polyvinylpyrrolidone (PVP), polyethylene glycol (PEG) and derivatives thereof, poly(N-isopropylacrylamide), tannic acid, dextran, dimercaptosuccinic acid (DMSA) and combinations thereof.

18. The system of claim 16, wherein the at least one nanoparticle is at least one magnetic nanoparticle selected from the group consisting of gold, ferric oxide, magnetite, maghemite, gadolinium-doped cobalt ferrite, and combinations thereof.

19. The system of claim 16, wherein the at least one nanoparticle has a size of from about 5 nm to about 100 nm.

20. The system of claim 16, wherein the at least one nanoparticle has a diameter of from about 5 nm to about 270 nm.

* * * * *